United States Patent
Hendrickson et al.

(10) Patent No.: US 10,188,085 B2
(45) Date of Patent: *Jan. 29, 2019

(54) SYSTEM AND METHODOLOGY FOR CULTURING COCHINEAL INSECTS ON AN ARTIFICIAL MEDIUM

(71) Applicant: Badderloch Woad, Inc., Irving, TX (US)

(72) Inventors: Constance M. Hendrickson, Irving, TX (US); Denise Lynn Merkle, Ft. Worth, TX (US)

(73) Assignee: SciConsult, Inc., Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/299,344

(22) Filed: Oct. 20, 2016

(65) Prior Publication Data
US 2017/0035036 A1    Feb. 9, 2017

Related U.S. Application Data

(63) Continuation-in-part of application No. 14/549,232, filed on Nov. 20, 2014, now Pat. No. 9,497,946, which is a continuation-in-part of application No. 13/867,321, filed on Apr. 22, 2013, now Pat. No. 8,919,281, which is a continuation-in-part of application No. 12/713,796, filed on Feb. 26, 2010, now Pat. No. 8,445,282, which is a continuation-in-part of application No. PCT/US2008/010013, filed on Aug. 22, 2008.

(60) Provisional application No. 60/967,148, filed on Aug. 31, 2007.

(51) Int. Cl.
| | |
|---|---|
| *A01K 67/033* | (2006.01) |
| *A23K 20/163* | (2016.01) |
| *A23K 50/90* | (2016.01) |
| *C12N 5/00* | (2006.01) |

(52) U.S. Cl.
CPC .......... *A01K 67/033* (2013.01); *A23K 20/163* (2016.05); *A23K 50/90* (2016.05); *C12N 5/0062* (2013.01); *C12N 2500/34* (2013.01); *C12N 2500/82* (2013.01)

(58) Field of Classification Search
CPC ..................................................... A01K 67/033
See application file for complete search history.

(56) References Cited

U.S. PATENT DOCUMENTS

| | | | |
|---|---|---|---|
| 6,293,223 B1 * | 9/2001 | Blossey | A01K 67/033 119/6.5 |
| 9,497,946 B2 * | 11/2016 | Hendrickson | A01K 67/033 |

FOREIGN PATENT DOCUMENTS

EP    1669414 A1 *    6/2006    ............. A61K 8/602

* cited by examiner

*Primary Examiner* — Rosanne Kosson
(74) *Attorney, Agent, or Firm* — John A. Fortkort; Fortkort & Houston PC

(57) ABSTRACT

A method is provided for culturing cochineal insects. In accordance with the method, a medium is created (101-109) from a mixture comprising a plant or cactus additive and a polymeric material. The medium is then inoculated (111) with a species selected from the group consisting of the genus *Dactylopius*.

19 Claims, 1 Drawing Sheet

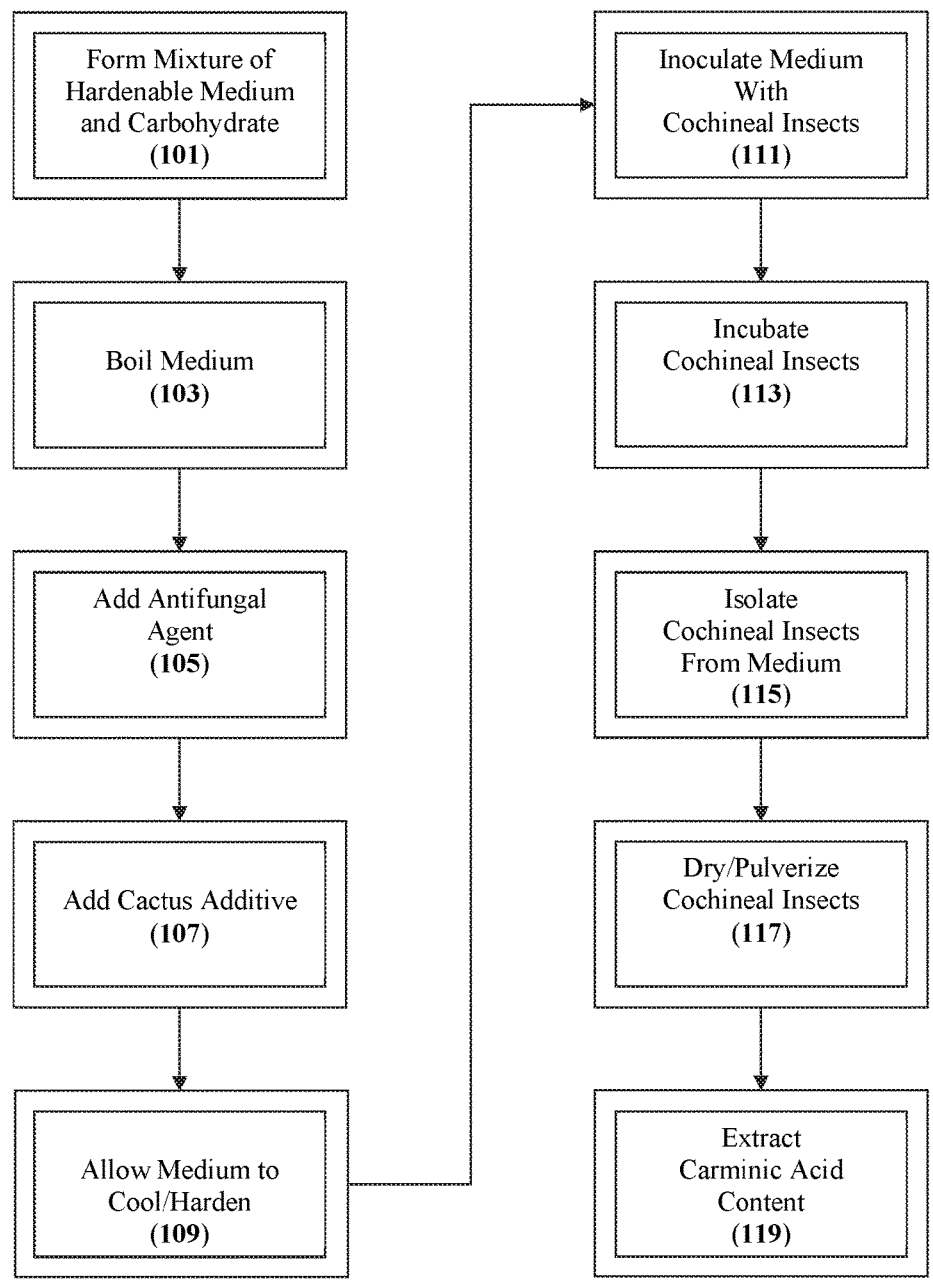

SYSTEM AND METHODOLOGY FOR CULTURING COCHINEAL INSECTS ON AN ARTIFICIAL MEDIUM

CROSS REFERENCE TO RELATED APPLICATIONS

This application is a continuation-in-part application which claims the benefit of priority from U.S. application Ser. No. 14/549,232, filed Nov. 20, 2014, having the same inventors, now allowed, and which is incorporated herein by reference in its entirety; which application is a continuation application of U.S. application Ser. No. 13/867,321, filed Apr. 22, 2013, having the same inventors, now allowed, and which is incorporated herein by reference in its entirety; which application is a continuation-in-part application of U.S. application Ser. No. 12/713,796, filed Feb. 26, 2010, having the same inventors, which issued as U.S. Pat. No. 8,445,282 on May 21, 2013, and which is incorporated herein by reference in its entirety; which application is a continuation-in-part application of PCT/US2008/010013, filed Aug. 22, 2008, having the same inventors, and which is incorporated herein by reference in its entirety; and which application claims the benefit of U.S. provisional application 60/967,148, filed Aug. 31, 2007, having the same inventors, and which is incorporated herein by reference in its entirety.

FIELD OF THE DISCLOSURE

The present disclosure relates generally to methods for incubating cochineal insects, and more particularly to methods for incubating cochineal insects in an artificial culture medium.

BACKGROUND OF THE DISCLOSURE

Carmine (also called cochineal) is a deep red, naturally occurring dye which has been used for thousands of years by populations in Central and North America. Despite the difficulty of producing carmine, the colorant is still in wide-spread demand. Carmine is an FDA approved additive, and is used to enhance the appearance of food, confections, pharmaceuticals and cosmetics. In addition, its staining properties make it an excellent contrasting agent for microbiological studies and cellular research. Carminic acid (see STRUCTURE I below), which is the dominant chromophoric ingredient in carmine, is naturally produced during the life cycle of female insects of the genus *Dactylopius*, such as those of the species *Dactylopius coccus* (referred to herein as cochineal insects).

STRUCTURE I

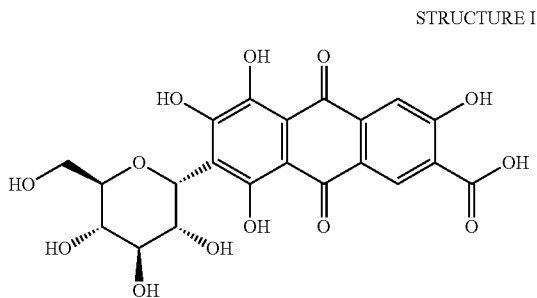 [SMILES: O=C(O)c1cc2c(cc1O)C(=O)c1c(O)c(O)c([C@H]3O[C@H](CO)[C@@H](O)[C@H](O)[C@H]3O)c(O)c1C2=O]

Cochineal insects occur naturally as parasites on cacti of the genus *Opuntia*, with *Opuntia ficus-indica* being the most suitable host. At present, cultivation of cochineal insects for large scale harvest is initiated through careful inoculation of cacti with infected cactus pads or with pathogen-free females. Typically, the insects are introduced to the host via baskets known as Zapotec nests. After inoculation, the cochineal insects must be protected from predators and from harmful weather conditions during their 3 month growth cycle.

Carmine is then laboriously extracted from the tiny (about 0.2 inch or 0.5 cm in length) female cochineal insects after the pads of the inoculated cacti are gathered. Approximately 155,000 insects are required to yield a single kg of carminic acid. The harvesting process is a labor and time intensive endeavor, and typically involves removing the cochineal insects by hand from the infected cactus pads.

The yield of cochineal insects (and hence carmine) may be adversely affected by the presence of various naturally occurring predators to the insects, as well as by cold temperatures or rainy conditions. Moreover, cochineal insect cultivation and yields are dependent on the health of the *Opuntia* host. This aspect of cochineal farming is especially challenging, since cochineal insects are parasites which are capable of killing the host cactus. Consequently, cochineal farmers must ensure that a large supply (typically more than 10,000 acres) of cactus host is sustained at all times.

In light of the aforementioned difficulties attendant to cochineal cultivation, there is a need in the art for a method for harvesting cochineal insects that overcomes these problems. In particular, there is a need in the art for a method for cultivating cochineal insects that is less labor, time and resource intensive, and which is not geographically limited. These and other needs may be met by the methodologies, compositions and devices disclosed herein and hereinafter described.

SUMMARY OF THE DISCLOSURE

In one aspect, a method is provided herein for cultivating cochineal insects. In accordance with the method, a medium is created from a mixture comprising a vegetable or cactus additive and a (preferably curable or hardenable) polymeric material. The medium is then inoculated with a species selected from the group consisting of the genus *Dactylopius*. In some embodiments, the medium may be dried or dehydrated, either before or after inoculation.

In another aspect, a method for cultivating cochineal insects is provided. The method comprises (a) heating a mixture comprising (i) a cactus additive obtained from a cactus of the genus *Opuntia*, (ii) a polysaccharide, and (iii) glucose; (b) combining the mixture with a three-dimensional matrix; (c) cooling the mixture to form a hardened medium; and (d) inoculating the hardened medium with a species selected from the group consisting of the genus *Dactylopius*.

In a further aspect, a composition is provided which comprises a plant or cactus additive and a polymeric material, wherein the medium is inoculated with a species selected from the group consisting of the genus *Dactylopius*.

BRIEF DESCRIPTION OF THE DRAWINGS

FIG. 1 is a flowchart illustrating an embodiment of a method for producing carminic acid from cochineal insects in accordance with the teachings herein.

DETAILED DESCRIPTION

It has now been found that the aforementioned needs may be met by cultivating cochineal insects, or other species selected from the genus *Dactylopius*, in a suitable artificial medium. Such an artificial medium may be fabricated, for example, from a curable or hardenable medium which contains a cactus additive such as, for example, cactus pulp, cactus nectar, or cactus powder. Preferably, the cactus additive is obtained from the genus *Opuntia*. The curable or hardenable medium may itself be derived from a carbohydrate and a suitable polysaccharide stock. Preferably, the carbohydrate is a monosaccharide, and even more preferably, the carbohydrate is glucose. Corn syrup is an especially preferred source of the carbohydrate. The polysaccharide stock may comprise a material such as Agar, agarose, agaropectin, carrageenan, or other suitable polysaccharides.

Cultivation of cochineal insects in an artificial medium of the type described herein is highly advantageous in that the insects may be grown in a controlled environment where they are free from predation, and in which growth conditions may be controlled or optimized to produce maximum yields. Moreover, this approach removes the need to utilize *Opuntia* (cactus) as the host for the cochineal insect, and thus removes many of the geographical and climactic considerations from cochineal cultivation.

The cochineal insects may be harvested by isolating them from the artificial medium. The method by which the insects are isolated may depend on the particular medium utilized, and may include, without limitation, filtration or isolation based on gravimetric considerations. In the case of agar, for example, isolation of the insects may be accomplished by first dissolving the hardened medium in the presence of a suitable solvent (preferably with heating), followed by filtration of the resulting mixture.

The carminic acid content may be removed from the isolated insects through a suitable chemical extraction process. Alternatively, in some embodiments, the medium may be dehydrated (as, for example, by placing it in a desiccator) prior to extraction therefrom of the insects and/or the carminic acid content. Such embodiments offer the advantage that the dehydrated medium, which may, for example, be in the form of one or more "chips" or plugs, or which may be pulverized into a particulate mass or powder, can be easily handled, and extraction operations may be readily performed thereon.

The following examples illustrate the preparation and inoculation with cochineal insects of artificial media of the type described herein.

EXAMPLE 1

The following example illustrates the preparation of one particular, non-limiting embodiment of a culture medium for cochineal insects in accordance with the teachings herein. Aseptic culture conditions and aseptic techniques were used throughout.

A base medium was prepared by mixing 2.25 L water with 60-88 g Agar and 0-350 mL light corn syrup (see step 101 of FIG. 1). The resulting mixture was heated to clarity, and sterilized by boiling (see step 103 of FIG. 1). The mixture was then cooled to about 180° F., after which an antifungal agent was added to the mixture (see step 105 of FIG. 1). In some embodiments, the antifungal agent was nyastatin, which was added at a ratio of about 4.8 mL per 200 mL of base medium. In other embodiments, the antifungal agent was methyl paraben, which was added at a ratio of about 0.2 g per 200 mL base medium.

Next, one or more of the prickly pear additives from TABLE 1 below was added to the mixture (see step 107 of FIG. 1) in the indicated percent by weight.

TABLE 1

Prickly Pear Additives

| Prickly Pear Additive | Percent by Weight |
| --- | --- |
| prickly pear nectar | 5-25 |
| prickly pear pulp | 5-25 |
| prickly pear powder | 0.5-5 |

The resulting media was then poured into a suitable receptacle and allowed to cool and harden (see step 109 of FIG. 1). In some embodiments, this receptacle was a series of sterile Petri plates, while in other embodiments, the receptacle was a sterile culture container. In some embodiments, the receptacle contained a sterile, 3-dimensional matrix, such as a sponge, *luffa* (a fibrous matrix obtained from tropical and subtropical vines of the genus *Luffa*), a cellulosic screen, a nylon screen, or another suitable support matrix.

EXAMPLE 2

The following example illustrates a particular, non-limiting embodiment of a method for inoculating and incubating a culture medium of the type described herein with cochineal insects.

The media from EXAMPLE 1 was allowed to harden at room temperature, and was then inoculated (see step 111 of FIG. 1) aseptically with active cottony scale (cochineal) colonies. The colonies were removed from cottony scale-infested prickly pear leaves which were harvested in the wild. No prickly pear tissue was transferred to the culture medium. The cultures were then incubated at room temperature (see step 113 of FIG. 1) and in ambient light until growth of cottony scale cultures was observed.

After culture medium preparation (which, in some embodiments, may be followed by partial or full dehydration and/or pulverization of the medium) and inoculation as described above, the cochineal insects may be incubated for a suitable period of time before they are harvested. The incubation period may vary. However, the cochineal insects are typically harvested when the insects are from about 70 to about 110 days old, preferably when the insects are from about 80 to about 100 days old, more preferably when the insects are from about 85 to about 95 days old, and most preferably when the insects are about 90 days old. Of course, it will be appreciated that the insects can propagate over a longer term and that, in some embodiments of the methodologies described herein, even longer periods of incubation may be utilized.

The temperature range utilized for incubation may also vary. Preferably, the cochineal insects are incubated at a temperature within the range of about 20° C. to about 35° C., more preferably at a temperature within the range of about 25° C. to about 30° C., and most preferably at a temperature of about 23° C.

After a suitable incubation period, the insects are isolated from the artificial medium (see step 115 of FIG. 1). This process may involve solvation of the medium with a suitable solvent or solvent mixture, heating the medium sufficiently to soften the medium or to improve its flow characteristics (e.g., by reducing its viscosity), inducing the chemical or physical degradation of the medium, or other such processes. For example, the artificial medium may be melted or dissolved with a solvent to produce a liquid or solution which can then be filtered through a Buchner funnel, a glass frit, a portion of metal mesh, a particulate bedding, a cellulosic substrate, a column, or another suitable porous medium to effect removal of the insects (or their carminic acid content) therefrom. In some embodiments, the removal process may include scraping or washing one or more surfaces of the artificial medium, or the use of centrifugation or other means of separation or fractionation.

After the cochineal insects have been isolated from the artificial medium, the insects are then preferably dried and pulverized into a powder (see step 117 of FIG. 1). Drying the insects may be advantageous in increasing the shelf life of the insect remains or any powders made therefrom, and may also aid in the extraction process. Preferably, the insects are dried to a weight that is about 20% to about 40% of their original body weight, and more preferably, the insects are dried to a weight that is about 25% to about 35% of their original body weight. Most preferably, the insects are dried to a weight that is about 30% of their original body weight.

The resulting powder is then boiled and filtered through a suitable filter medium to remove insoluble materials, and the carminic acid content is extracted by precipitating it from the filtered solution with a suitable precipitating agent (see step 117 of FIG. 1).

In some embodiments, the precipitating agent may have the chemical composition

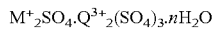

$$M^+{}_2SO_4 \cdot Q^{3+}{}_2(SO_4)_3 \cdot nH_2O$$

wherein Q is preferably selected from the group consisting of Al, Cr and Fe, wherein M is preferably selected from the group consisting of Li, Na, K, Rb, Cs, and $NH_4$, and wherein n is typically within the range of about 0 to about 50, preferably within the range of about 12 to about 36, more preferably within the range of about 18 to about 30, and most preferably about 24. As a specific example of such a precipitating agent, Q may be aluminum, M may be calcium, n may be about 24, and the precipitating agent may be added to the filtered solution to precipitate aluminum carminate therefrom. The choice of M and Q may both have a noticeable effect on the color of the resulting dye.

In other embodiments, alum, or a mixture of alum and lime, may be utilized as the precipitating agent. Prior to the addition of alum, one or more additives selected from the group consisting of stannous chloride, citric acid, borax, and gelatin may be added to the filtered solution. In still other embodiments, the precipitating agent may comprise a mixture of calcium hydroxide and alum.

In some variations of the process described above, after the cochineal insects have reached a suitable age, the medium may be partially or fully dehydrated. This process may be used to generate cultured "chips" or plugs of medium, which may facilitate handling, shipping or the subsequent extraction process. The insects may then be extracted from the dried medium. Alternatively, the carminic acid content of the insects may be extracted in situ. In some variations of this latter type of embodiment, dye extraction may be preceded by pulverization of the medium, which may be used to generate particulate masses or powders rich in carminic acid content. This dye content may then be readily extracted using chemical processes of the type described above.

In other embodiments, portions or plugs of media (which may be partially or fully dehydrated) supporting viable cochineal insects may be used to transfer cultures to fresh media. This method of culture transfer may be used to transfer cultures between media residing in local or remote locations. For example, this method of culture transfer is amenable to shipping of the cultures, since it is possible to maintain the cochineal insects in a viable state in such a sample for prolonged periods of time.

In some embodiments of the methodologies described herein, the uninoculated, gelled media may be dehydrated for ease of shipping or storage. The dehydrated media may then be rehydrated in a suitable solution or liquid prior to, or during, innoculation.

As previously noted, various ingredients may be incorporated into the media used to culture cochineal insects in accordance with the teachings herein. These ingredients preferably include a cactus additive, which may comprise cactus nectar, cactus pulp, or powdered cactus. The cactus additive may be derived from a species selected from the group consisting of *Opuntia amyclaea*, *Opuntia atropes*, *Opuntia cantabrigiensis*, *Opuntia brasilienis*, *Opuntia ficus-indica*, *Opuntia fuliginosa*, *Opuntia jaliscana*, *Opuntia leucotricha*, *Opuntia lindheimeri*, *Opuntia microdasys*, *Opuntia megacantha*, *Opuntia pilifera*, *Opuntia rob usta*, *Opuntia sarca*, *Opuntia schikendantzii*, *Opuntia stricta*, *Opuntia streptacantha*, and *Opuntia tomentosa*. Preferably, the cactus additive is derived from *Opuntia ficus-indica*. In some embodiments, the growth medium may contain various other pulps, juices, powders, and extracts from other plant materials including, but not limited to, those derived from species of the genera *Scleranthus*, *Hieracium*, *Silene*, *Agrostis*, *Caragana*, *Herniaria*, *Potentilla*, *Fragaria*, *Cerastium*, and *Cucurbita*.

Various other ingredients may also be used in the culture medium. In some embodiments, these other ingredients may be used in place of, or in conjunction with, cactus additives. Such ingredients may include, without limitation, various plant pulps, extracts, or other plant additives, especially those derived from the genus *Cucurbita*, including squashes, gourds, potatoes or pumpkins. The use of acorn squash pulp is particularly preferred. Such ingredients may also include tannins (especially wine tannins), green tea extracts, gallic acid and its derivatives, phytosterols, and inoditol hexaphosphate. Such ingredients also include pulps, extracts, powders, and other products obtained from various parts of plants from the *Musa* genera in the family Musaceae (which includes bananas and plantains) including, without limitation, such products obtained from the foliage, stalks, flowers, fruit, roots and sap thereof, and particularly including banana powder, banana peel powder, or plantain flour. In some embodiments, these ingredients may be dried or dehydrated prior to use, and may be formulated into a powdered mixture of agar, cellulose, or other materials to form pre-made media.

The curable or hardenable medium may itself be derived from a carbohydrate and/or a suitable polysaccharide stock. Preferably, the carbohydrate is a monosaccharide, and even more preferably, the carbohydrate is glucose. Corn syrup is an especially preferred source of the carbohydrate in those embodiments which utilize one, though it is important to note that various embodiments are possible which do not utilize corn syrup or any other sugars. The polysaccharide stock may comprise a material such as Agar, agarose, agaropectin, carrageenan, or other suitable polysaccharides. In some embodiments, a gelling agent may be utilized to produce a curable or hardenable medium.

In some embodiments, various waxes may be utilized in the curable or hardenable medium, either in addition to, or in place of, a carbohydrate and/or polysaccharide. Suitable waxes include, for example, beeswax, Chinese wax, lanolin was, shellac wax, spermaceti, various plant waxes (including, for example, soy wax, Candelilla wax, coconut wax and carnauba wax), and various petroleum waxes (including for example, paraffin waxes, which are typically mixtures of saturated n- and iso-alkanes, naphthenes, and alkyl- and naphthene-substituted aromatic compounds).

In some embodiments, various hydrogels may be utilized in the curable or hardenable medium, either in addition to, or in place of, a carbohydrate and/or polysaccharide. Suitable hydrogels include, for example, those described in Enas M. Ahmed, "Hydrogel: Preparation, Characterization, and Applications: A Review", Journal of Advanced Research (2015) 6, 105-121, which is incorporated herein by reference in its entirety. In other embodiments, poly-lactic acid may be utilized in the curable or hardenable medium, either in addition to, or in place of, a carbohydrate and/or polysaccharide. Poly-lactic acid, and methods for making it, are described, for example, in M. Shidian, et al., "Poly-Lactic Acid: Production, Applications, Nanocomposites, and Release Studies", Comprehensive Reviews in Food Science and Food Safety, Vol. 9, 2010, which is incorporated herein by reference in its entirety. Still other embodiments may feature growth media which comprise one or more polymeric materials selected from the group consisting of ABS, acetals, cellulosics, epoxies, fluorocarbons, nylon, phenolics, polycarbonates, polyesters, polyethylenes, polypropylenes, polystyrenes, and polyvinyl chloride.

In some embodiments, various non-nutritive additives or matrices may be utilized for hydration or to impart structure, configuration, texture, or mechanical strength to the media. Such non-nutritive additives include, but are not limited to, silica, alumina, clay, diatomaceous earth, and various two- or three-dimensional matrices, such as sponge, *luffa* (a fibrous matrix obtained from tropical and subtropical vines of the genus *Luffa*), cellulosic screens, fibrous pads or matrices (including, without limitation, steel wool and its plastic counterparts), steel or plastic scrubbies, or nylon screens. In some embodiments utilizing matrices, the insects may be removed from the matrix, and the matrix may be reused.

Various antifungal, antibacterial or antimicrobial agents may be used in the compositions and methodologies described herein. Suitable antifungal agents include nystatin, methyl paraben, polygodial, anethole, benzoic acid, propionic acid, sorbic acid, hexanoic acid, methyl sorbate, miconazole, and the like, or various combinations or subcombinations of the foregoing. The use of natural antifungal agents is preferred. In some cases, the use of two or more antifungal agents may yield synergistic effects. For example, the fungicidal activity of polygodial may be increased by using it in conjunction with sublethal amounts (typically at an equivalent of ½ MFC) of anethole, or by using anethole in conjunction with sub-lethal amounts of polygodial. Similarly, the fungicidal activity of sorbic acid may be enhanced by using it in combination with sub-lethal amounts of polygodial, while the fungicidal activity of polygodial may be enhanced by using it in combination with sub-lethal amounts of sorbic acid. Suitable antimicrobial agents may include, without limitation, resveratrol; quinolones; flavones, flavonoids, and flavanols; tannins; terpenoids; and other essential oils.

The use of antifungal agents is particularly desirable in the initial transfer of cochineal insects (or the eggs or colonies thereof) to the culture medium, since fungal growth is sometimes observed to occur in the transferred material. For example, a spray or misting of a suitable antifungal agent may be employed shortly before or after transfer of inoculation materials to the culture medium. The antifungal agent may be applied to the inoculation materials, to the culture medium, or to both. In some embodiments, a suitable antimicrobial agent may be incorporated into the culture medium.

In some embodiments of the systems and methodologies disclosed herein, the surface of the growth medium may be textured so as, for example, to impart a pattern to it or a desired level or roughness or smoothness. By way of example, it has been found to be helpful to the growth of cochineal insects to texture the surface of the growth medium in a way that mimics the surface of natural prickly pear. Suitable methods which may be utilized to pattern the growth medium include, for example, the use of molds or soft lithography. Suitable methods of using soft lithography for this purpose are described in R. Kane et al., "Patterning Proteins and Cells Using Soft Lithography", Biomaterials 20 (1999) 2363-2376, which is incorporated herein by reference in its entirety.

Preferably, the surface growth medium is neither too wet nor too sticky (tacky). In the former case, it is often found that the cochineal insects are unable or unwilling to reproduce, and in some cases, are unable to live. In the latter case, it is often found that the cochineal insects are unable to function properly, thereby decreasing the efficiency of the culture method. Surface moisture may be added via direct methods, or may be adjusted by maintaining appropriate humidity levels in the environment of the growth medium. Tackiness may be a function of surface wetness, or controlled by the composition of the growth media. The relationship of cochineal growth to surface wetness/tackiness of the growth media is shown in TABLE 2 below. Preferably, the surface tackiness which is within the range of about 20% to about 80%, more preferably within the range of about 20% to about 60%, and most preferably within the range of about 30% to about 50%.

TABLE 2

Relationship of Cochineal Growth to Surface Wetness/tackiness of Media

| Wetness/Tackiness | Cochineal Health |
|---|---|
| 100% wetness/0% tackiness | Minimal growth |
| 80 | Better |
| 60 | Good |
| 40 | Best |
| 20 | Good |
| 0% wetness/100% tackiness | dead/stuck |

Preferably, the humidity of the environment for the growth media is maintained within a range of about 30% to about 80%, more preferably within a range of about 40% to about 75%, and most preferably within a range of about 50% to about 65%. Appropriate humidity may be maintained through misting, or via stand-alone humidifiers or those integral to the air handling systems. Humidifying solutions are preferably clean or sterile, and may contain nutrients, antimicrobial agents, growth factors, and other ingredients.

The temperature of the environment of the growth media may also be an important factor in the growth and health of cochineal insects. Preferably, this temperature is within the range of 20-30° C. (68-86° F.).

Various substrates, structures or substrate enhancers may be incorporated into the growth media or into/onto the pans, trays or container in which the growth media is placed. Suitable substrates may be soaked/impregnated, coated, or otherwise treated with growth media to support cochineal growth, although it is not required that all surfaces be coated with media. Smooth or patterned treated materials, such as cardboard, paper or wood, may be utilized. Suitable substrates or substrate enhancers may also include hooked or looped surfaces (such as, for example, VELCRO™ hook-and-loop type fasteners), nylon or plastic meshes or netting, natural or artificial sponges, foamed or porous materials, natural or artificial grasses, leaves or mosses, structures integral to the growing pans, such as those pulled from molten plastics or waxes, glochids scraped from wet prickly pear or shredded or dried prickly pear, prickles derived from carapaces of animals (chitin/chitosan, which may have the added benefit of being antimicrobial), shredded or cut paper, especially if devoid of synthetic dyes, and shredded or intact fabrics, especially if rough or bumpy, such as slubbed silk or corduroy.

The growth medium, while requiring components of specific function, may be tailored to support insect growth, as well as to promote culture health, insect health, and to potentially shorten insect life cycle for the purposes of increasing carminic acid/carmine yield. The growth medium may contain suitable additives, such as food sources, antimicrobial agents, and growth factors, and these additives may also be present in the media or in the humidifying solutions that are used to maintain the cultures within optimal growing conditions.

In some embodiments of the systems and methodologies described herein, growth factors may be utilized to encourage the development of cochineal insects and to decrease the length of life cycles. Such growth factors include, but are not limited to, polyphenols such as gallic acid, resveratrol, tannins and tannic acid.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims.

What is claimed is:

1. A self-supporting mass, comprising:
an artificial culture medium which contains a plant additive and which has been inoculated with a plurality of insects selected from the group consisting of the genus *Dactylopius*;
wherein said artificial culture medium further comprises a three-dimensional matrix.

2. The self-supporting mass of claim 1, wherein said plant additive is selected from the group consisting of cactus pulp, cactus powder and cactus nectar.

3. The self-supporting mass of claim 2, wherein said plant additive is obtained from a genus selected from the group consisting of *Opuntia, Musaceae, Scleranthus, Hieracium, Silene, Agrostis, Caragana, Herniaria, Potentilla, Fragaria, Cerastium*, and *Cucurbita*.

4. The self-supporting mass of claim 3, wherein said plant additive is obtained from the genus *Opuntia*.

5. The self-supporting mass of claim 3, wherein said plant additive is obtained from the species *Opuntia ficus-indica*.

6. The self-supporting mass of claim 3, wherein said plant additive is obtained from the genus *Musaceae*.

7. The self-supporting mass of claim 1, wherein said artificial culture medium comprises a liquid that has been cured or hardened.

8. The self-supporting mass of claim 1, wherein said medium further comprises glucose.

9. The self-supporting mass of claim 8, wherein said medium further comprises a monosaccharide and a polysaccharide.

10. The self-supporting mass of claim 9, wherein said monosaccharide is glucose.

11. The self-supporting mass of claim 9, wherein said polysaccharide is selected from the group consisting of Agar, agarose, agaropectin and carrageenan.

12. The self-supporting mass of claim 1, wherein said medium is dehydrated.

13. The self-supporting mass of claim 1, wherein said medium comprises an antifungal agent.

14. The self-supporting mass of claim 13, wherein said antifungal agent is selected from the group consisting of nystatin, methyl paraben, polygodial, anethole, benzoic acid, propionic acid, sorbic acid, hexanoic acid, methyl sorbate, and miconazole.

15. The self-supporting mass of claim 1, wherein said three-dimensional matrix is selected from the group consisting of sponge, *luffa*, cellulosic screening and nylon screening.

16. The self-supporting mass of claim 1, wherein said three-dimensional matrix is cellulosic screening.

17. The self-supporting mass of claim 1, wherein said self-supporting mass further comprises a material selected from the group consisting of polyphenols, resveratrol, tannins and tannic acid.

18. The self-supporting mass of claim 1, wherein said self-supporting mass has a surface tackiness which is within the range of about 30% to about 50%.

19. The self-supporting mass of claim 1, wherein said self-supporting mass further comprises one or more polyphenols.

* * * * *